(12) United States Patent
Kawahara et al.

(10) Patent No.: US 11,224,622 B2
(45) Date of Patent: Jan. 18, 2022

(54) AGENT FOR PREVENTING OR TREATING FAT-ASSOCIATED DISEASES AND/OR INFLAMMATION

(71) Applicants: Biofermin Pharmaceutical Co., Ltd., Kobe (JP); Public University Corporation Yokohama City University, Yokohama (JP)

(72) Inventors: Tomohiro Kawahara, Kobe (JP); Yoshiki Tanaka, Kobe (JP); Masaki Shimakawa, Kobe (JP); Hiroshi Ohno, Kobe (JP); Takaomi Kessoku, Yokohama (JP); Atsushi Nakajima, Yokohama (JP)

(73) Assignees: Biofermin Pharmaceutical Co., Ltd., Kobe (JP); Public University Corporation Yokohama City University, Yokohama (JP)

( * ) Notice: Subject to any disclaimer, the term of this patent is extended or adjusted under 35 U.S.C. 154(b) by 42 days.

(21) Appl. No.: 16/621,650

(22) PCT Filed: Jun. 15, 2018

(86) PCT No.: PCT/JP2018/022865
§ 371 (c)(1),
(2) Date: Dec. 11, 2019

(87) PCT Pub. No.: WO2018/230695
PCT Pub. Date: Dec. 20, 2018

(65) Prior Publication Data
US 2021/0145897 A1 May 20, 2021

(30) Foreign Application Priority Data
Jun. 16, 2017 (JP) .............................. JP2017-118686

(51) Int. Cl.
*A61K 35/741* (2015.01)
*A61K 35/00* (2006.01)
*A23L 33/135* (2016.01)

(52) U.S. Cl.
CPC .......... *A61K 35/741* (2013.01); *A23L 33/135* (2016.08); *A61K 2035/115* (2013.01)

(58) Field of Classification Search
None
See application file for complete search history.

(56) References Cited

U.S. PATENT DOCUMENTS

| 2015/0044172 A1 | 2/2015 | Bicalho et al. |
| 2019/0030089 A1* | 1/2019 | Langella ................... A61P 1/00 |

FOREIGN PATENT DOCUMENTS

| JP | 2016-511272 A | 4/2016 |
| JP | 2016-517425 A | 6/2016 |
| WO | WO 2014/137211 A1 | 9/2014 |
| WO | WO 2014/152338 A1 | 9/2014 |
| WO | WO 2016/065279 A1 | 4/2016 |
| WO | WO 2016/141454 A1 | 9/2016 |
| WO | WO 2017/072278 A1 | 5/2017 |
| WO | WO 2017/210428 A1 | 12/2017 |

OTHER PUBLICATIONS

Altamimi, M. et al., "Effect of oligosaccharides on the adhesion of gut bacteria to human HT-29 cells" Anaerobe, 2016, pp. 136-142, vol. 39.
Duncan, Sylvia H. et al., "Growth requirements and fermentation products of Fusobacterium prausnitzii, and a proposal to reclassify it as *Faecalibacterium prausnitzii* gen. nov., comb. Nov." International Journal of Systematic and Evolutionary Microbiology, 2002, pp. 2141-2146, vol. 52.
Martin, Rebeca et al., "Impact of the Commensal Bacterium Faecalibacterium prausnitzii in a Non Active Inflammation Murine Model" Gastroenterology, 2013, pp. S897-S898, vol. 144, No. 5.
Sokol, Harry et al., "Faecalibacterium prausnitzii is an anti-inflammatory commensal bacterium identified by gut microbiota analysis of Crohn disease patients" PNAS, Oct. 2008, pp. 16731-16736, vol. 105, No. 43.
International Search Report for PCT/JP2018/022865 dated Sep. 11, 2018.
Extended European Search Report dated Feb. 8, 2021 in European Application No. 18818703.3, in 15 pages.
Lopez-Siles et al., "Cultured Representatives of Two Major Phylogroups of Human Colonic Faecalibacterium prausnitzii Can Utilize Pectin, Uronic Acids, and Host-Derived Substrates for Growth", *Appl. Environ. Microbiol.*, vol. 78, No. 2, 2012, in 10 pages.
Munukka et al., "*Faecalibacterium prausnitzii* treatment improves hepatic health and reduces adipose tissue inflammation in high-fat fed mice". *The ISME Jounral*, vol. 11, 2017, pp. 166-1679.
Qui et al., "*Faecalibacterium prausnitzii* upregulates regulatory T cells and anti-inflammatory cytokines in treating TNBS-induced colitis", *Journal of Crohn's and Colitis*, vol. 7, 2013, pp. e558-e568.
International Preliminary Report on Patentability for PCT/JP2018/022865 dated Dec. 17, 2019.
Hippe B. et al. "Faecalibacterium prausnitzii phylotypes in type two diabetic, obese, and lean control subjects." Beneficial Microbes, Apr. 6, 2016, vol. 7, No. 4, pp. 511-517.

(Continued)

*Primary Examiner* — Sarvamangala Devi
(74) *Attorney, Agent, or Firm* — Knobbe Martens Olson & Bear LLP

(57) ABSTRACT

An object of the present invention is to provide an agent for preventing or treating a fat-associated disease and/or inflammation. The present invention provides an agent for preventing or treating a fat-associated disease and/or inflammation, the agent comprising a *Faecalibacterium* bacterium or a processed product thereof.

7 Claims, 12 Drawing Sheets
Specification includes a Sequence Listing.

(56) References Cited

OTHER PUBLICATIONS

Search Report and Written Opinion dated Mar. 29, 2021, corresponding to Singapore Patent Application No. 11201911301W.
Zhang M. et al. "Faecalibacterium prausnitzii Inhibits Interleukin-17 to Ameliorate Colorectal Colitis in Rats." PLOS ONE, Oct. 2, 2014, vol. 9, No. 10, pp. e109146.
Nakajima, Atsushi "Microbiome in NAFLD" Journal of Intestinal Microbiology, 2017, vol. 31, Issue 2.

* cited by examiner

Data = mean ± SEM, **; $p < 0.01$ (vs normal group),
; $p < 0.01$ (vs control group), n = 9-10

Data = mean ± SEM, **; p < 0.01 (vs normal group),
; p < 0.01 (vs control group), n = 9-10

Data = mean ± SEM, *; p < 0.05 (vs normal group), n = 9-10

Data = mean ± SEM, **; $p < 0.01$ (vs normal group),
; $p < 0.01$ (vs control group), n = 9-10

Data = mean ± SEM, **; p < 0.01 (vs normal group),
; p < 0.05 (vs control group), n = 9-10

Data = mean ± SEM, **; p < 0.01 (vs normal group), n = 9-10

AGENT FOR PREVENTING OR TREATING FAT-ASSOCIATED DISEASES AND/OR INFLAMMATION

CROSS REFERENCE TO RELATED APPLICATIONS

This application is a U.S. National Phase Application of PCT International Application Number PCT/JP2018/022865, filed on Jun. 15, 2018, designating the United States of America and published in the Japanese language, which is an International Application of and claims the benefit of priority to Japanese Patent Application No. 2017-118686, filed on Jun. 16, 2017. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-IWAT019-002APC.txt, the date of creation of the ASCII text file is Oct. 31, 2019, and the size of the ASCII text file is 3 KB.

TECHNICAL FIELD

The present invention relates to an agent for preventing or treating a fat-associated disease and/or inflammation, the agent comprising a *Faecalibacterium* bacterium or a processed product thereof.

BACKGROUND ART

Eating habits have changed in recent years and today we have an abundance of food. Excessive calorie intake along with a lack of regular physical activity has contributed to rapid increase in those who suffer from metabolic syndrome. Metabolic syndrome, also called "visceral fat syndrome", is associated with various diseases and abnormalities, including lipid metabolic abnormalities and carbohydrate metabolic abnormalities. Those with metabolic syndrome are highly likely to develop symptoms and diseases, such as arteriosclerosis, fatty liver, hyperlipemia, obesity, hypertension and diabetes mellitus.

The fatty liver is mainly caused by excessive drinking and hypernutrition. Non-alcoholic fatty liver disease (hereinafter also called NAFLD) displays liver disease-like symptoms not caused by drinking. NAFLD was considered as a benign non-progressive disease and was not regarded as of importance. However, the number of the cases that develop hepatitis, cirrhosis, liver cancer and other diseases has been increasing, which makes NAFLD non-negligible.

Various types of medicines have been developed to prevent or treat metabolic syndrome, but many of them have strong adverse effects and cannot be continuously used for a long period of time.

SUMMARY OF INVENTION

Technical Problem

An object of the present invention is to provide an agent for preventing or treating a fat-associated disease and/or inflammation, and/or fibrosis.

Solution to Problem

The inventors conducted extensive research to solve the above problems, and as a result found that *Faecalibacterium* bacteria have preventive or therapeutic effect on fat-associated diseases and/or inflammation. The inventors made further studies and discovered many new findings to complete the present invention.

That is, the present invention relates to the following.

(1) An agent for preventing or treating a fat-associated disease and/or inflammation, the agent comprising a *Faecalibacterium* bacterium or a processed product thereof.

(2) The agent according to the above (1), wherein the fat-associated disease is a metabolic syndrome-associated disease or non-alcoholic fatty liver disease (NAFLD).

(3) The agent according to the above (1) or (2), wherein the *Faecalibacterium* bacterium is *Faecalibacterium prausnitzii* ATCC (registered trademark) 27768, *Faecalibacterium prausnitzii* ATCC 27766, or *Faecalibacterium prausnitzii* TY-2 (Accession No. NITE BP-02743).

(4) A composition for preventing or treating a fat-associated disease and/or inflammation, the composition comprising the agent according to any one of the above (1) to (3).

(5) The composition according to the above (4), which is any of a pharmaceutical composition, a food composition and a cosmetic composition.

(6) Use of a *Faecalibacterium* bacterium or a processed product thereof for production of the agent or composition according to any one of the above (1) to (5).

(7) *Faecalibacterium prausnitzii* TY-2 (Accession No. NITE BP-02743) or a processed product thereof.

(8) A method for preventing or treating a fat-associated disease and/or inflammation, the method comprising administering a *Faecalibacterium* bacterium or a processed product thereof to a human or a non-human animal.

(8-2) The method according to the above (8), wherein the fat-associated disease is a metabolic syndrome-associated disease or non-alcoholic fatty liver disease (NAFLD).

(8-3) The method according to the above (8) or (8-2), wherein the *Faecalibacterium* bacterium is *Faecalibacterium prausnitzii* ATCC (registered trademark) 27768, *Faecalibacterium prausnitzii* ATCC 27766, or *Faecalibacterium prausnitzii* TY-2 (Accession No. NITE BP-02743).

(9) Use of a *Faecalibacterium* bacterium or a processed product thereof for prevention or treatment of a fat-associated disease and/or inflammation.

(9-2) The use according to the above (9), wherein the fat-associated disease is a metabolic syndrome-associated disease or non-alcoholic fatty liver disease (NAFLD).

(9-3) The use according to the above (9) or (9-2), wherein the *Faecalibacterium* bacterium is *Faecalibacterium prausnitzii* ATCC (registered trademark) 27768, *Faecalibacterium prausnitzii* ATCC 27766, or *Faecalibacterium prausnitzii* TY-2 (Accession No. NITE BP-02743).

(10) A *Faecalibacterium* bacterium or a processed product thereof for use in prevention or treatment of a fat-associated disease and/or inflammation.

(10-2) The *Faecalibacterium* bacterium or a processed product thereof for use according to the above (10), wherein the fat-associated disease is a metabolic syndrome-associated disease or non-alcoholic fatty liver disease (NAFLD).

(10-3) The *Faecalibacterium* bacterium or a processed product thereof for use according to the above (10) or (10-2), wherein the *Faecalibacterium* bacterium is *Faecalibacterium prausnitzii* ATCC 27768, *Faecalibacterium prausnitzii* ATCC 27766, or *Faecalibacterium prausnitzii* TY-2 (Accession No. NITE BP-02743).

Advantageous Effects of Invention

The present invention provides an agent for preventing or treating a fat-associated disease and/or inflammation.

DESCRIPTION OF EMBODIMENTS

*Faecalibacterium* Bacteria

Figure 1:
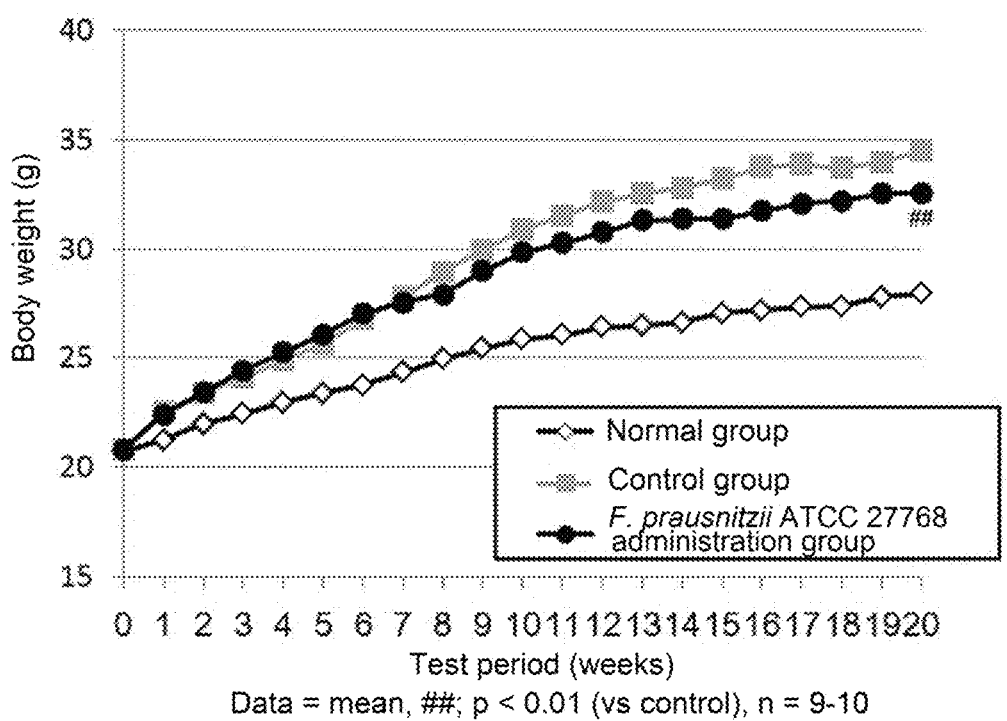
FIG. 1 is a chart showing the change in the body weight of test animals in the normal group, the control group and the *F. prausnitzii* ATCC 27768 administration group.

The *Faecalibacterium* bacteria used in the present invention are not limited to a particular one, and may be, for example, *Faecalibacterium prausnitzii* etc. *Faecalibacterium prausnitzii* may include, for example, *Faecalibacterium prausnitzii* ATCC 27768, *Faecalibacterium prausnitzii* ATCC 27766, *Faecalibacterium prausnitzii* TY-2 (Accession No. NITE BP-02743), etc. The *Faecalibacterium* bacteria used in the present invention may further include bacteria that are identified to be identical or substantially identical to known *Faecalibacterium* bacteria based on the comparison of the characteristics, including, for example, morphological characteristics (for example, the shape of colonies, the shape of cells, etc.), physiological or biochemical characteristics (for example, utilization of sugars, growth temperature, optimal pH, etc.), and chemotaxonomic characteristics (fatty acid composition of bacterial cells, etc.). The *Faecalibacterium* bacteria used in the present invention may further include bacteria that are identified to be identical or substantially identical to known *Faecalibacterium* bacteria based on nucleotide sequence analysis of 16S rRNA genes.

Isolation and Culture Methods of *Faecalibacterium* Bacteria

The *Faecalibacterium* bacteria may be isolated by any method, and may be isolated from, for example, the feces etc. of a human or a non-human animal by known methods or methods known per se (see, for example, Example 1 described herein); or may be isolated from the natural environment or a living body; or may be purchased from organizations, such as ATCC; or may be purchased as commercially available bacteria.

*Faecalibacterium prausnitzii* TY-2 (Accession No. NITE BP-02743) was deposited with Patent Microorganisms Depositary (NPMD), Biological Resource Center, Incorporated Administrative Agency National Institute of Technology and Evaluation (address: #122, 2-5-8 Kazusakamatari, Kisarazu-shi, Chiba 292-0818, Japan) on Jun. 11, 2018 as an international deposit under the Budapest Treaty.

The bacteria can be obtained from the depository center by submitting the request. Alternatively, the bacteria may be those that are identified to be identical or substantially identical to *Faecalibacterium prausnitzii* TY-2 (Accession No. NITE BP-02743) based on the comparison of the characteristics, including, for example, morphological characteristics (for example, the shape of colonies, the shape of cells, etc.), physiological or biochemical characteristics (for example, utilization of sugars, growth temperature, optimal pH, etc.), and chemotaxonomic characteristics (fatty acid composition of bacterial cells, etc.). The bacteria may be those that are identified to be identical or substantially identical to *Faecalibacterium prausnitzii* TY-2 (Accession No. NITE BP-02743) based on nucleotide sequence analysis of 16S rRNA genes.

The *Faecalibacterium* bacteria may be cultured by known methods or methods known per se in accordance with the present invention. The *Faecalibacterium* bacteria may be cultured in a commercially available medium in an incubator.

Bacteria or Processed Products Thereof

The *Faecalibacterium* bacteria of the present invention (including *Faecalibacterium prausnitzii* TY-2 (Accession No. NITE BP-02743) etc. as described above; hereinafter the same applies) are preferably viable bacterial cells, but a processed product of bacteria may also be used. The processed product of bacteria refers to a product produced by subjecting *Faecalibacterium* bacteria to certain processing, and the processing is not limited to a particular one. Specific examples of the processed product include disrupted cell suspension prepared by, for example, sonicating bacterial cells; culture medium or culture supernatant of bacterial cells; solid residues isolated from such disrupted cell suspension, culture medium or culture supernatant by solid-liquid separation method, such as filtration or centrifugation; etc. The processed product also includes processed solution produced by removing cell walls by enzymatic or mechanical treatment; bacterial cell components, such as protein complexes (proteins, lipoproteins, glycoproteins, etc.) or peptide complexes (peptides, glycopeptides, etc.), obtained by trichloroacetic acid treatment or salting-out method; extracellular products secreted by bacteria outside their cell membrane; etc. The processed product further includes concentrates, diluted products, or dried products of these. The processed product of the present invention also includes a further processed product of disrupted cell suspension prepared by, for example, sonicating bacterial cells; a further processed product of culture medium or culture supernatant of bacterial cells, etc., and such a further processed product can be prepared by subjecting the disrupted cell suspension or culture medium or culture supernatant to, for example, separation by various chromatography, etc. The processed product of the present invention further includes viable cells or dead cells of the *Faecalibacterium* bacteria of the present invention. The dead bacterial cells can be prepared by, for example, enzymatic treatment, heat-treatment at about 100° C., drug treatment such as antibiotics, chemical treatment such as formalin, radiation treatment such as γ-rays, etc.

The bacteria used in the present invention may be a dried product (dried bacterial cells), and are preferably single micron-sized dried bacterial cells. The term "dried bacterial cells" typically refers to individual dried bacterial cells or a gathered mass of dried bacterial cells. The term "single micron-sized" refers to a size of 1 to 10 µm when rounded to the nearest whole number. When the *Faecalibacterium* bacteria used in the present invention are in the form of single micron-sized dried bacterial cells, the proportion of viable bacteria in a bacterial formulation is high, and therefore the formulation highly effectively prevents or treats a fat-associated disease and/or inflammation.

A preferred production method of the dried bacterial cells will be described below. Bacterial cells as described above are dispersed in a solvent to prepare a bacterial cell liquid. The solvent may be a known solvent in the art, but is preferably water. If desired, ethanol may be added. When the bacteria in a solvent containing ethanol is subjected to drying, ethanol evaporates first and water then evaporates, which enables gradual drying. The bacterial cell liquid may be in the form of a suspension. The solvent may be the same as described above. When the bacteria are suspended in a solvent, a suspending agent such as sodium alginate may be used.

An additive conventionally used in the art, including, for example, a protective agent, an excipient, a binder, a disintegrant and an antistatic, may be added to the bacterial cell liquid in a usual amount.

The dried bacterial cells may be produced by drying the bacterial cell liquid with a spray dryer. The spray dryer is preferably equipped with an atomization device capable of forming single micron-sized spray droplets. Spray droplets with a very small particle diameter will have a large surface area per unit mass, and therefore the spray droplets efficiently contact with warm air for drying and in turn the productivity improves.

The term "single micron-sized liquid droplets" refers to spray droplets having a particle diameter of 1 to 10 µm when rounded to the nearest whole number.

Examples of the spray dryer include a spray dryer equipped with an atomization device that may be, for example, a rotary atomizer (a rotary disk), a pressure nozzle, or a two-fluid or four-fluid nozzle utilizing the force of compressed gas.

The spray dryer may be any type that is capable of forming single micron-sized spray droplets and has any type of atomization device as exemplified above. Preferred is a spray dryer equipped with a four-fluid nozzle.

In such a spray dryer equipped with a four-fluid nozzle, the four-fluid nozzle may have a structure in which a gas passage is combined with a liquid passage to form a single unit, and two sets of the unit are symmetrically disposed at the edge of the nozzle, thereby providing the nozzle edge with slopes for directing the flow of a fluid.

The spray dryer is preferably equipped with an external mixing atomization device capable of directing compressed gas and liquid from both sides to collide at a single focal point at the tip of the nozzle edge. This type of atomization device is advantageous in that nozzle clogging is prevented and spraying can be performed for a long period of time.

Examples of the compressed gas include inert gas, such as air, carbon dioxide gas, nitrogen gas, argon gas, etc. Especially when easily oxidized materials or the like are spray-dried, inert gas such as carbon dioxide gas, nitrogen gas, argon gas, etc. is preferred.

The pressure of the compressed gas is usually about 1 to 15 kgf/cm$^2$, preferably about 3 to 8 kgf/cm$^2$.

The gas flow rate at the nozzle is usually about 1 to 100 L/min, preferably about 10 to 20 L/min, per mm of the nozzle edge.

Typically, after spraying, the spray droplets are allowed to contact with warm air for drying in a drying chamber to evaporate the moisture to give dried bacterial cells.

The inlet temperature of the drying chamber is usually about 2 to 400° C., preferably about 5 to 250° C., and more preferably about 5 to 150° C. Even when the inlet temperature is as high as about 200 to 400° C., the temperature in the drying chamber does not become excessively high due to heat of evaporation of moisture. The death of or damage to living bacteria can be prevented to some extent by reducing the retention time in the drying chamber.

The outlet temperature is usually about 0 to 120° C., preferably about 5 to 90° C., and more preferably about 5 to 70° C.

Reduction in the particle diameter of the dried bacterial cells as described above increases the proportion of viable bacteria in a bacterial formulation, which advantageously provides a formulation with a high proportion of viable bacteria.

In other words, the bacterial cell liquid is preferably sprayed into single micron-sized spray droplets to produce single micron-sized dried bacterial cells. Spray droplets with a small particle diameter will have a large surface area per unit mass, and therefore the spray droplets efficiently contact with warm air for drying, and in turn the death of or damage to bacterial cells due to the heat from warm air for drying is prevented to the best extent possible. As a result, the proportion of viable bacteria is increased, and dried bacterial cells contain a large number of viable bacteria.

Agent

The agent of the present invention comprises a *Faecalibacterium* bacterium or a processed product thereof. The agent can be used for prevention or treatment of a fat-associated disease and/or inflammation.

The fat-associated disease may be, for example, a fat-related disease or a disease that is developed or affected in association with a fat-related disease. The fat-related disease may be, for example, a disease that is developed or aggravated by fat accumulation. Examples of the disease that is developed or aggravated by fat accumulation include metabolic syndrome, non-alcoholic fatty liver disease (NAFLD) (including non-alcoholic steatohepatitis (NASH)), and hyperlipemia. Metabolic syndrome is a condition that includes a cluster of diseases and abnormalities. Examples of the diseases and abnormalities include obesity (for example, lipid metabolic abnormalities, fatty liver, etc.), carbohydrate metabolic abnormalities, abnormal insulin resistance, heart diseases such as angina pectoris and myocardial infarction, arteriosclerotic diseases (for example, cerebral infarction, arteriosclerosis obliterans, etc.), etc. Examples of the disease that is developed or affected in association with a fat-related disease include cirrhosis, liver cancer, etc.

The inflammation is not limited to a particular type, and may be, for example, spontaneous inflammation, or lasting inflammation, etc. The site of the inflammation may be the whole body or part of the body etc. The cause of the inflammation is not limited to particular one, and may be, for example, an external cause or an internal cause. Examples of the external cause include physical factors (for example, mechanical stimulus, heat, ultraviolet rays, etc.), chemical factors (for example, strong acids, strong alkalis, harmful chemicals, etc.), biological factors (for example, bacteria, viruses, parasites, etc.), etc. Examples of the internal cause include allergies, autoimmune disorders (for example, atopic dermatitis, rheumatoid arthritis, etc.), production of inflammation substances (for example, endotoxin), functional disorders of organs, stress (for example, tendovaginitis, osteoarthritis), etc. The degree of the inflammation is not limited to a particular one, and may be ranges, for example, from mild to severe.

The effect of the agent of the present invention to prevent or treat a fat-associated disease and/or inflammation can be determined by known methods or methods known per se. In an example, when the body weight measurement or the analysis of the amount of liver fat, the fat around the epididymis, etc. by CT scan etc. indicates reduction in the body weight or the fat amounts, the agent is determined to have the effect of preventing or improving obesity. In another example, when the pathological analysis of part of liver tissue for examination of lipid droplets and/or fibrosis indicates reduced lipid droplets and/or fibrosis, the agent is determined to have the effect of preventing or treating fatty liver and/or liver fibrosis. In another example, when the analysis of the expression of a gene involved in fibrosis of hepatocytes by quantitative real-time PCR etc. indicates reduced gene expression, the agent is determined to have the effect of preventing or treating liver fibrosis. The quantitative real-time PCR can be performed using, for example, fluorescent-labeled TaqMan probe, Molecular Beacon, etc. TaqMan probe and Molecular Beacon are an oligonucleotide probe that has a homology with an internal sequence in the region to be amplified by PCR and is labeled with a fluorescent dye and a quencher. TaqMan probe and Molecular Beacon can be used in PCR reaction. In another example, when the measurement of the plasma levels of total cholesterol, ALT and AST indicates reduced levels of them, the agent is determined to have the effect of maintaining or improving liver function. In another example, when HOMA-IR calculated from the plasma levels of glucose and insulin by the formula (1) below indicates reduced HOMA-IR levels, the agent is determined to have the effect of improving glucose tolerance: formula (1): HOMA-IR=fasting plasma insulin (µIU/mL)×fasting plasma glucose (mg/dL)/405.

In another example, when the measurement of the plasma levels of endotoxin indicates reduced plasma levels of endotoxin, the agent is determined to have the effect of preventing or treating inflammation. In another example, when the analysis of the gene expression of proinflammatory cytokines etc. found in the plasma indicates reduced gene expression of the proinflammatory cytokines etc., the agent is determined to have the effect of preventing or treating inflammation.

The term "prevention" as used herein includes inhibition of development and progression of a disease, etc., and the degree of inhibition is not limited to a particular one. The term "treatment" includes improvement etc. and the degree of improvement is not limited to a particular one. The "treatment" also includes remission of a disease and complete recovery from a disease, etc.

The agent of the present invention is only required to contain a *Faecalibacterium* bacterium or a processed product thereof, and may further contain as appropriate another ingredient depending on the dosage form, the mode of administration, the desired efficacy, etc. Examples of said another ingredient include another pharmacologically active ingredient, a carrier, and an additive (for example, a preservative, a surfactant, a stabilizer, an isotonic agent, a pH adjuster, etc.). These ingredients may be used alone or in combination of two or more types.

Administration Method, Dosage Form, Etc. of the Agent

The mode of administration (or the dosage form) of the agent of the present invention may be any mode of administration (or any dosage form) as long as the agent can be used to prevent or treat a fat-associated disease and/or inflammation. The agent may be administered, for example, via an oral route (as an oral agent) or a parenteral route (as a parenteral agent), etc.

The oral agent may be prepared by, for example, combining the agent of the present invention with a pharmaceutically acceptable carrier. Examples of the oral agent include, for example, solid dosage forms, such as tablets (for example, sugar-coated tablets etc.), pills, capsules, powders, coated tablets, granules, and troches; liquid dosage forms, such as solutions, suspensions, emulsions, syrups and elixirs; semi-solid dosage forms, such as jelly preparations; etc. Examples of the parenteral agent include, for example, injections (for example, subcutaneous, intravenous, intramuscular, and intraperitoneal injections, intravenous drips, etc.), suppositories (for example, rectal suppositories, vaginal suppositories, etc.), topical agents (for example, transdermal preparations, ointments, transnasal preparations, etc.), etc.

The dosage form of the agent of the present invention is not limited to a particular one, and may be, for example, a liquid, a fluid, a gel, a semi-solid, a solid, etc. The dosage form also includes liquids, fluids, gels, semi-solids, solids and other dosage forms that are prepared at the time of use.

Dosage of the Agent

The amount of the bacteria or a processed product thereof contained in the agent of the present invention is not limited to a particular amount, but the amount calculated based on the dry mass of the bacteria may be, for example, about 0.0001% by mass to about 50% by mass, about 0.001% by mass to about 30% by mass, about 0.01% by mass to about 10% by mass, or the like relative to the total mass of the agent, and the amount calculated based on the dry mass of a processed product of the bacteria may be, for example, about 0.0001% by mass to about 50% by mass, about 0.001% by mass to about 30% by mass, about 0.01% by mass to about 10% by mass, or the like relative to the total mass of the agent.

The dose of the agent of the present invention may be selected as appropriate depending on the dosage form, the route of administration, the subject of administration, the age and body weight of the subject, the intervals of administration, etc. The dose of the agent when administered via an oral route may depend on the subject of administration (for example, an adult human), the intervals of administration (for example, one dose a day), etc., but the oral dose of the agent calculated based on the dry mass of the bacteria of the present invention may be, for example, about 0.0001 mg to about 100 g, about 0.001 mg to about 50 g, about 0.01 mg to about 20 g, about 0.1 mg to about 5 g, or the like, or the oral dose of the agent calculated based on the dry mass of a processed product of the bacteria of the present invention may be, for example, about 0.0001 mg to about 100 g, about 0.001 mg to about 50 g, about 0.01 mg to about 20 g, about 0.1 mg to about 5 g, or the like. When the agent of the present invention contains viable bacteria, the dose of the agent calculated based on the number of viable bacteria is, for example, typically about 1 to $10^{12}$ cells/dose per adult human, preferably $10^1$ to $10^{11}$ cells/dose per adult human, and more preferably $10^2$ to $10^{10}$ cells/dose per adult human. The number of viable bacteria contained in the formulation is determined by an appropriate method depending on the type of bacteria, but can be easily determined by, for example, the plate culture method using tryptic soy agar plates with 5% defibrinated sheep blood as described later. The dose of the agent when administered via a parenteral route may depend on the subject of administration (for example, an adult human), the intervals of administration (for example, one dose a day), etc., but the parenteral dose of the agent calculated based on the dry mass of the bacteria of the present invention may be, for example, about 0.0001 mg to about 100 g, about 0.001 mg to about 50 g, about 0.01 mg to about 20 g, about 0.1 mg to about 5 g, or the like, or the parenteral dose of the agent calculated based on the dry mass of a processed product of the bacteria of the present invention may be, for example, about 0.0001 mg to about 100 g, about 0.001 mg to about 50 g, about 0.01 mg to about 20 g, about 0.1 mg to about 5 g, or the like.

The intervals of administration are also selected as appropriate depending on the dosage form, the subject of administration, etc., and the agent may be administered, for example, about 1 to 3 times a day, or about 1 to 3 times every several months.

The frequency of administration is also selected as appropriate depending on the dosage form, the subject of administration, etc., and the agent may be administered in a single dose or continuously administered at certain intervals.

The agent of the present invention can be used to prepare various types of formulations (compositions, pharmaceutical compositions, food compositions, or cosmetic compositions) according to various embodiments. The present invention therefore includes such a composition containing the agent.

Medicament (Pharmaceutical Composition)

The present invention can be used to prepare a medicament comprising the agent of the present invention.

The medicament of the present invention may be produced by any method in which the agent of the present invention is used as an ingredient, and the production method may be a known conventional method or a method known per se.

The mode of administration (or the dosage form) of the medicament of the present invention may be any mode of administration (or any dosage form) as long as the medicament can be used to prevent or treat a fat-associated disease and/or inflammation. The medicament may be administered, for example, via an oral route (as an oral medicament) or a parenteral route (as a parenteral medicament), etc.

The oral medicament may be prepared by, for example, combining the agent of the present invention with a pharmaceutically acceptable carrier. Examples of the oral medicament include, for example, solid dosage forms, such as tablets (for example, sugar-coated tablets etc.), pills, capsules, powders, coated tablets, granules, and troches; liquid dosage forms, such as solutions, suspensions, emulsions, syrups and elixirs; semi-solid dosage forms, such as jelly preparations; etc. Examples of the parenteral medicament include, for example, injections (for example, subcutaneous, intravenous, intramuscular, and intraperitoneal injections, intravenous drips, etc.), suppositories (for example, rectal suppositories, vaginal suppositories, etc.), topical medicaments (for example, transdermal preparations, ointments, transnasal preparations, etc.), etc.

The dosage form of the medicament of the present invention is not limited to a particular one, and may be, for example, a liquid, a fluid, a gel, a semi-solid, a solid, etc. The dosage form also includes liquids, fluids, gels, semi-solids, solids and other dosage forms that are prepared at the time of use.

The amount of the bacteria or a processed product thereof contained in the medicament of the present invention is not limited to a particular amount, but the amount calculated based on the dry mass of the bacteria may be, for example, about 0.0001% by mass to about 50% by mass, about 0.001% by mass to about 30% by mass, about 0.01% by mass to about 10% by mass, or the like relative to the total mass of the medicament, and the amount calculated based on the dry mass of a processed product of the bacteria may be, for example, about 0.0001% by mass to about 50% by mass, about 0.001% by mass to about 30% by mass, about 0.01% by mass to about 10% by mass, or the like relative to the total mass of the medicament.

The dose of the medicament of the present invention may be selected as appropriate depending on the dosage form, the route of administration, the subject of administration, the age and body weight of the subject, the intervals of administration, etc. The dose of the medicament when administered via an oral route may depend on the subject of administration (for example, an adult human), the intervals of administration (for example, one dose a day), etc., but the oral dose of the medicament calculated based on the dry mass of the bacteria of the present invention may be, for example, about 0.0001 mg to about 10 g, about 0.001 mg to about 5 g, about 0.01 mg to about 1 g, about 0.1 mg to about 500 mg, or the like, or the oral dose of the medicament calculated based on the dry mass of a processed product of the bacteria of the present invention may be, for example, about 0.0001 mg to about 10 g, about 0.001 mg to about 5 g, about 0.01 mg to about 1 g, about 0.1 mg to about 500 mg, or the like. The dose of the medicament when administered via a parenteral route may depend on the subject of administration (for example, an adult human), the intervals of administration (for example, one dose a day), etc., but the parenteral dose of the medicament calculated based on the dry mass of the bacteria of the present invention may be, for example, about 0.0001 mg to about 10 g, about 0.001 mg to about 5 g, about 0.01 mg to about 1 g, about 0.1 mg to about 500 mg, or the like, or the parenteral dose of the medicament calculated based on the dry mass of a processed product of the bacteria of the present invention may be, for example, about 0.0001 mg to about 10 g, about 0.001 mg to about 5 g, about 0.01 mg to about 1 g, about 0.1 mg to about 500 mg, or the like.

The intervals of administration are also selected as appropriate depending on the dosage form, the subject of administration, etc., and the medicament may be administered, for example, about 1 to 3 times a day, or about 1 to 3 times every several months.

The frequency of administration is also selected as appropriate depending on the dosage form, the subject of administration, etc., and the medicament may be administered in a single dose or continuously administered at certain intervals.

The medicament of the present invention, in any dosage form, can contain, in addition to the agent of the present invention, a pharmaceutically acceptable base material or carrier (for example, an aqueous solvent, a solid carrier, a polyalcohol, a vegetable oil, an oil base, etc.), a pharmaceutically acceptable additive (for example, a surfactant, a flavor or cooling agent, an antiseptic, a bactericide or antibacterial agent, a pH adjusting agent, a tonicity agent, a chelating agent, a buffering agent, a stabilizer, an antioxidant, a thickening agent, etc.), a physiologically active ingredient other than the agent of the present invention (for example, a vitamin, an amino acid, a sugar, a high molecular weight compound, etc.), a pharmacologically active ingredient (for example, an antibacterial ingredient, a bactericide ingredient, etc.), etc.

Food Product (Food Composition)

The agent of the present invention can be used in the field of food products. That is, the agent of the present invention may be a food additive etc. Such a food additive can be used to prepare a food product. The present invention therefore also includes a food product (a food composition) containing the agent.

Examples of the food product include food and drink products, such as supplemental foods, balanced nutritional foods, health foods, foods with nutrient function claims, foods for specified health use, foods with functional claims, and foods for patients. These food and drink products may be produced by any method that allows the food and drink products to exhibit the effect of preventing or improving a fat-associated disease and/or inflammation. Specific examples of suitable food products include supplements in the form of a powder, granules, a capsule, a tablet, etc. In addition to the food products in the form as described above, the foods and drinks also include, for example, fermented foods (dairy products) such as yogurt and cheese; confectionaries such as chewing gums, hard candies, gummy candies, tablet candies, cookies, cakes, chocolate, ice cream, jelly, mousse, pudding, biscuits, corn flakes, chewable tablets, wafers, and rice crackers; drinks such as carbonated drinks, soft drinks, milk beverages, coffee drinks, black tea drinks, fruit juice drinks, nutritional drinks, alcoholic drinks, and mineral water; powdered drinks such as powdered juice and powdered soup; seasonings such as dressing and sauce; bread; noodles; steamed fish paste such as fish cake; and rice seasonings. Besides such forms for oral intake, the food product may be in the form for enteral intake (a liquid food, etc.).

The amount of the agent contained in the food product of the present invention can be selected as appropriate depending on the age, sex and health conditions of the subject and other conditions, and adjusted as appropriate for the dose, the form of the food product, or the like. The food product of the present invention containing a large amount of the agent of the present invention can also be provided to allow the agent to effectively exhibit its ameliorative or preventive effect.

The food product of the present invention may be produced by any method in which the agent of the present invention is used as an ingredient, and the production method may be a known conventional method or a method known per se. In the process of production of the food product of the present invention, the agent of the present invention may be added or blended by conventional methods.

The amount of the agent contained in the food product of the present invention is not limited to a particular amount, and can be adjusted as appropriate depending on the type of the food product, the ingredients of the food product, etc.

The amount of the agent of the present invention to be ingested in the form of the food product of the present invention is not limited to a particular amount, and can be adjusted as appropriate depending on the subject of use, the age and sex of the subject, the type of food product, the ingredients of the food product, etc.

Cosmetic Product (Cosmetic Composition)

The agent of the present invention can be used in the field of cosmetics. The agent of the present invention has anti-inflammatory effect, and therefore a cosmetic product of the present invention comprising the agent of the present invention is capable of preventing or treating inflammation of the skin, etc.

The cosmetic product of the present invention may be any type of cosmetic product that comprises the agent of the present invention, and includes those classified into quasi-drugs, such as medicated cosmetics, according to the definitions in the Pharmaceutical Affairs Law.

The shape, form, usage, manner of use, etc. of the cosmetic product of the present invention are not limited to particular ones, and may be selected as appropriate depending on the subject of use, the age and sex of the subject, etc.

The cosmetic product of the present invention may be produced by any method in which the agent of the present invention is used as an ingredient, and the production method may be a known conventional method or a method known per se. The cosmetic product of the present invention may contain, in addition to the agent of the present invention, a base material or carrier that can typically be used in a cosmetic product, and may also contain, as needed, an additive (for example, an antioxidant, a surfactant, a thickener, a preservative, a pH adjusting agent, an antiseptic, a colorant, a fragrance, etc.) and/or another active ingredient (for example, a moisturizing ingredient, an anti-inflammatory ingredient, an anti-bacterial or bactericide ingredient, a vitamin, a cell-activating ingredient, a blood circulation-promoting ingredient, a keratin-softening ingredient, a skin-whitening ingredient, an astringent ingredient, etc.) to the extent that the effects of the present invention are exhibited.

The cosmetic product, food product and medicament of the present invention as described above can typically be packaged in a container, a bag, etc. in a conventional manner. The container, bag, etc. may be any container, bag, etc. that are usable as a container for a cosmetic product, a food product and a medicament, and may be selected as appropriate from those conventionally known or those known per se depending on the form, shape and dosage form of the agent, the cosmetic product, the food product and the medicament of the present invention.

The animal as a subject of the present invention may be a human or a non-human animal, and includes mammals, but is not limited thereto. Examples of mammals include primates such as humans, monkeys, orangutans, chimpanzees, and gorillas; experimental animals such as rabbits and rodents such as mice, rats, hamsters, and guinea pigs; domestic animals such as cow, horses, pigs, sheep, and goats; pets such as dogs and cats; and birds such as chickens, ducks and geese. The mammals are preferably primates (such as humans) or pets, more preferably humans, dogs or cats, and further preferably humans.

EXAMPLES

The present invention will be described in detail below with reference to Examples. The Examples are for illustrative purposes only, and the technical scope of the present invention is not limited thereto.

Preparation of Diluent Solution, Tryptic Soy Agar Plates with 5% Defibrinated Sheep Blood, and Tryptic Soy Broth with 5% Defibrinated Sheep Blood A diluent solution was prepared as described below in accordance with the method described in the "Bifidobacteria" section in the Japanese Pharmaceutical Codex. An amount of 6.0 g of disodium hydrogen phosphate anhydrous, 4.5 g of potassium dihydrogen phosphate, 0.5 g of polysorbate 80, 0.5 g of L-cysteine hydrochloride and 1.0 g of agar were combined in 1000 mL of purified water. The mixture was heat-sterilized at 121° C. for 15 minutes with a steam pressure sterilizer, and the pH was adjusted to 6.8 to 7.0.

Tryptic soy agar plates with 5% defibrinated sheep blood were prepared as follows. An amount of 40.0 g of Tryptic Soy Agar (Difco) was dissolved in 950 mL of distilled water and heat-sterilized at 121° C. for 15 minutes. The tryptic soy agar was allowed to cool down to about 47° C., and 50 mL of defibrinated sheep blood (Nippon Bio-Test Laboratories Inc.) was added. An appropriate amount of the tryptic soy agar was poured into sterilized petri plates to prepare tryptic soy agar plates with 5% defibrinated sheep blood (hereinafter may be called the agar plates A).

Tryptic soy broth with 5% defibrinated sheep blood was prepared as follows. An amount of 30.0 g of Tryptic Soy Broth (Wako Pure Chemical Industries, Ltd.) was dissolved in 950 mL of distilled water and heat-sterilized at 121° C. for 15 minutes. The tryptic soy broth (Wako Pure Chemical Industries, Ltd. or Nippon Bio-Test Laboratories Inc.) was allowed to cool down to about 47° C., and 50 mL of defibrinated sheep blood was added to prepare tryptic soy broth with 5% defibrinated sheep blood (hereinafter may be called the tryptic soy broth B).

The thus prepared diluent solution, tryptic soy agar plates and tryptic soy broth were used in the Examples described below.

Example 1: Isolation of *Faecalibacterium* Bacteria

To 900 µL of the diluent solution was added 100 mg of a human feces sample, and the mixture was mixed with a vortex mixer to obtain a homogeneous mixture. The mixture was 10-fold serially diluted in the diluent solution, and 100 µL of each of the diluted solutions was applied to the agar plates A using a cell spreader. Immediately after the application of the solutions, the agar plates A were incubated in an anaerobic incubator (Hirasawa Co. Ltd.) under anaerobic conditions at 37° C. for 48 to 96 hours to isolate colonies. At the end of the culture, the colonies established on the agar plates A were picked and streaked on fresh agar plates A with a toothpick and a loop, and the plates were immediately incubated under anaerobic conditions at 37° C. for 48 to 96 hours to obtain pure culture. This pure culture procedure was repeated again and the established colonies were scraped and suspended in an equal volume mixture of 20% glycerol and the culture broth, and stored at −80° C. A DNA was extracted by the conventional phenol extraction method, and homology analysis of 16S rRNA (16S ribosomal RNA) was performed to identify the bacterial species. All the procedures for isolation culture and pure culture were performed in an anaerobic chamber (Hirasawa Co. Ltd.).

Example 2: Preparation of Bacteria (*Faecalibacterium prausnitzii* Reference Strain ATCC 27768)

Centrifuged bacterial cells of *Faecalibacterium prausnitzii* reference strain ATCC 27768 (*F. prausnitzii* ATCC 27768) were prepared. Specifically, a cryopreserved strain of *F. prausnitzii* ATCC 27768 was subjected to stationary culture at 37° C. for 48 hours. The bacteria were inoculated into the tryptic soy broth B at a 1:100 volume ratio of the bacteria to the bacterial culture broth, and stationary culture was performed at 37° C. for 48 hours. The bacterial culture broth was centrifuged, and the bacterial pellet was washed twice with PBS, and centrifuged to give centrifuged bacterial cells.

Experimental Example A: Test Animals and Administration of Bacteria

C57BL/6J mice at 8 weeks old were given a high-fat high-fructose diet (may also be called AMLN diet; Research Diets, Inc.) and also orally given *F. prausnitzii* ATCC 27768 at a dose of 20 mg/animal once a day for 20 weeks. The normal group was given an ordinary diet (MF diet, Oriental Yeast Co., Ltd.) with no administration of *F. prausnitzii* ATCC 27768. The control group was given the high-fat high-fructose diet with no administration of *F. prausnitzii* ATCC 27768.

Example 3: Preventive or Therapeutic Effect on Metabolic Syndrome

Measurement of Body Weight, Diet Intake, Liver Weight and Weight of Fat Around the Epididymis During the test period, the body weight and the diet intake of the test animals were measured once a week in accordance with conventional methods.

At 20 weeks after the start of feeding with the AMLN diet, the animals were subjected to 18 hours of fasting, and the liver and the fat around the epididymis were harvested and weighed in accordance with conventional methods.

Blood Chemistry Analysis

Figure 2:
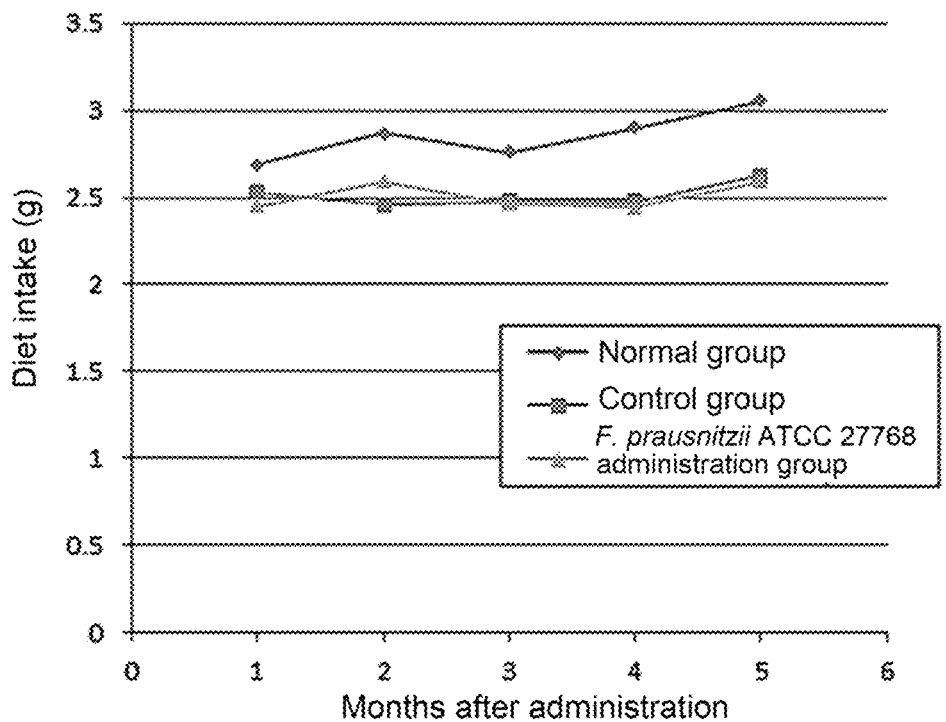
FIG. 2 is a chart showing the diet intake of test animals in the normal group, the control group and the *F. prausnitzii* ATCC 27768 administration group.
Figure 3:
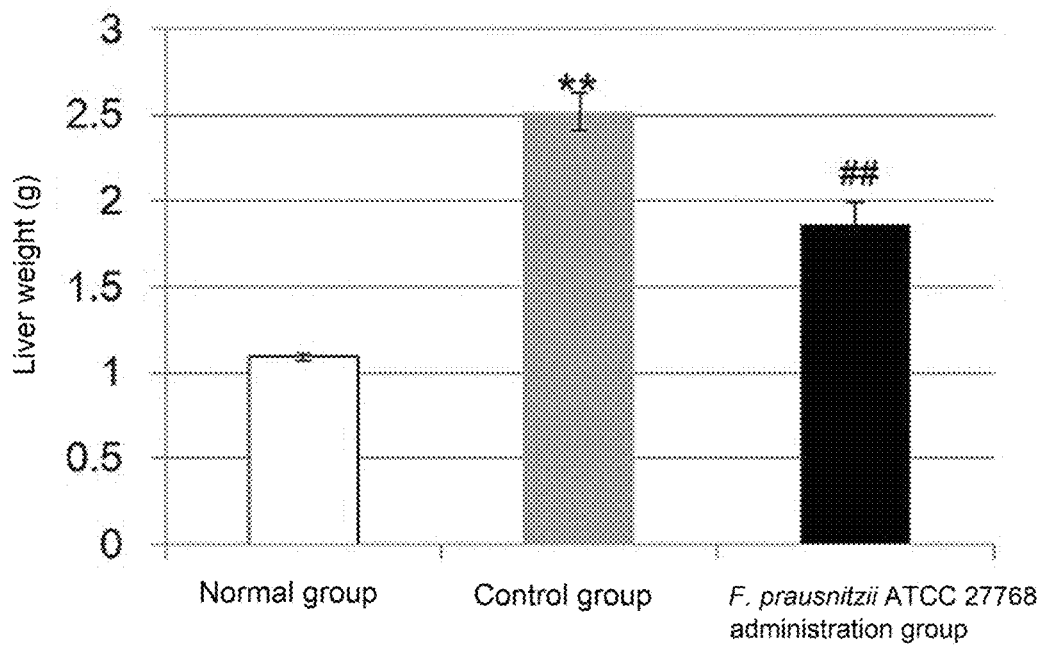
FIG. 3 is a chart showing the weight of the liver harvested from test animals in the normal group, the control group and the *F. prausnitzii* ATCC 27768 administration group.
Figure 4:
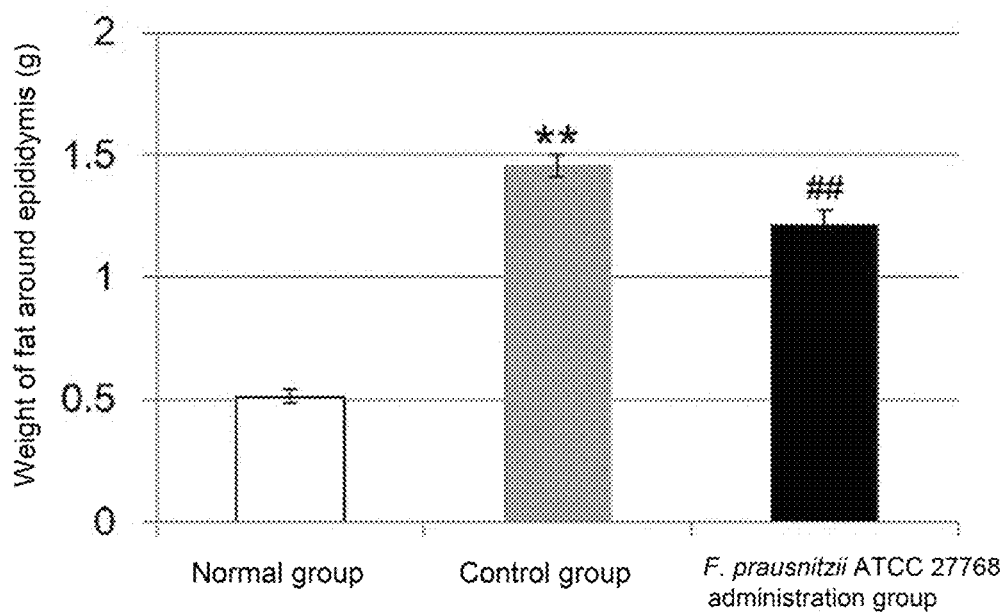
FIG. 4 is a chart showing the weight of the fat around the epididymis harvested from test animals in the normal group, the control group and the *F. prausnitzii* ATCC 27768 administration group.
Figure 5:
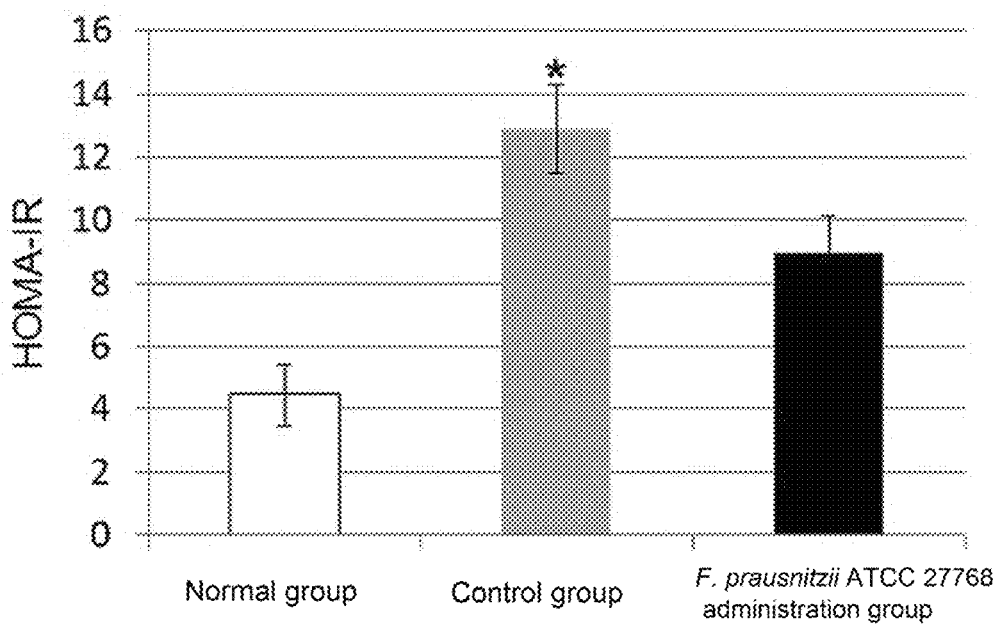
FIG. 5 is a chart showing the calculated HOMA-IR of test animals in the normal group, the control group and the *F. prausnitzii* ATCC 27768 administration group.

The plasma was separated from the whole blood withdrawn from the animals, and the plasma levels of glucose and insulin were measured with the glucose level measurement reagent, Glucose CII-Test Wako (Wako Pure Chemical Industries, Ltd.) and the insulin level measurement reagent, Ultra Sensitive Mouse Insulin Measurement Kit (Morinaga Institute of Biological Science, Inc.) according to the attached protocols. HOMA-IR was calculated using the above formula (1).
Results Increase in the body weight was significantly inhibited in the *F. prausnitzii* ATCC 27768 administration group as compared with the control group (FIG. 1). No difference was observed in the diet intake between the *F. prausnitzii* ATCC 27768 administration group and the control group (FIG. 2). The liver weight and the weight of the fat around the epididymis significantly increased in the control group as compared with the normal group (FIGS. 3 and 4). In contrast, increases in the liver weight and the weight of the fat around the epididymis by AMLN diet intake were significantly inhibited in the *F. prausnitzii* ATCC 27768 administration group (FIGS. 3 and 4). HOMA-IR, which is an indicator of insulin resistance, was significant improved by administration of *F. prausnitzii* ATCC 27768 (FIG. 5). The *F. prausnitzii* ATCC 27768 administration group showed the tendency of reduction in the insulin levels as compared with the control group.

These results indicate that *F. prausnitzii* ATCC 27768 has anti-obesity effect and glucose tolerance-improving effect. These results also indicate that administration of *F. prausnitzii* ATCC 27768 inhibits the progression of metabolic syndrome.

Example 4: Preventive or Therapeutic Effect on NAFLD Blood Chemistry Analysis

The plasma was separated from the whole blood withdrawn from the animals, and the plasma levels of total cholesterol, ALT and AST were determined by the external laboratory SRL, Inc. The levels of total cholesterol and triglyceride as lipid analysis in the liver were determined by the external laboratory Skylight Biotech, Inc.
Pathological Analysis The liver was harvested from the test animals, fixed by immersing in 10% formalin, embedded in paraffin to create a paraffin block, and sectioned into paraffin sections, according to conventional methods. The paraffin sections of the liver were stained with Oil red O staining stock solution (Muto Pure Chemicals Co., Ltd.) or Sirius red stain solution (Sigma-Aldrich Japan G.K.) according to the attached protocol. The stained paraffin sections were photographed.
Gene Expression Analysis A total RNA was extracted from the liver harvested from the test animals using an RNA extraction reagent (QIAGEN) according to the attached protocol. From the total RNA, a cDNA was generated using a reverse transcription reagent (Thermo Fisher Scientific Inc.) according to the attached protocol. Quantitative real-time PCR was performed using the cDNA as a template. For the quantitative real-time PCR, a real-time PCR reagent (Thermo Fisher Scientific Inc.) and a real-time PCR device (Thermo Fisher Scientific Inc.) were used according to the attached protocols. The gene expression levels of collagen 1α1, αSMA, TNFα and 18S rRNA were determined by the quantitative real-time PCR. The primers and probes for the collagen 1α1, αSMA and TNFα genes were those whose sequences are shown in Table 1. The gene expression levels of 18S rRNA were determined using Eukaryotic 18S rRNA Endogenous Control (VIC™/MGB (product name) probe, primer limited) (ABI, Inc., Cat. No: 4319413E). The gene expression levels were evaluated by calculating the relative expression levels of each gene normalized to that of 18S rRNA.

TABLE 1

| Collagen 1α1 | Probe | CCCGCCGATGTC GCTATCCAGCT | SEQ ID NO: 1 |
|---|---|---|---|
| | Forward | GACCGATGGATT CCCGTTCG | SEQ ID NO: 2 |
| | Reverse | GGACATTAGGCG CAGGAAGG | SEQ ID NO: 3 |
| αSMA | Probe | CCCAGAGTGGAGA AGCCCAGCCAGT | SEQ ID NO: 4 |
| | Forward | ACCCTTCAGCGTT CAGCCTC | SEQ ID NO: 5 |
| | Reverse | CACACATAGCTGG AGCAGCG | SEQ ID NO: 6 |
| TNFα | Probe | AGGGGCCACCACG CTCTTCTGTCTAC | SEQ ID NO: 7 |
| | Forward | GCCTATGTCTCAG CCTCTTCTC | SEQ ID NO: 8 |
| | Reverse | AGGCCATTTGGGA ACTTCTCATC | SEQ ID NO: 9 |

Results

Figure 6:
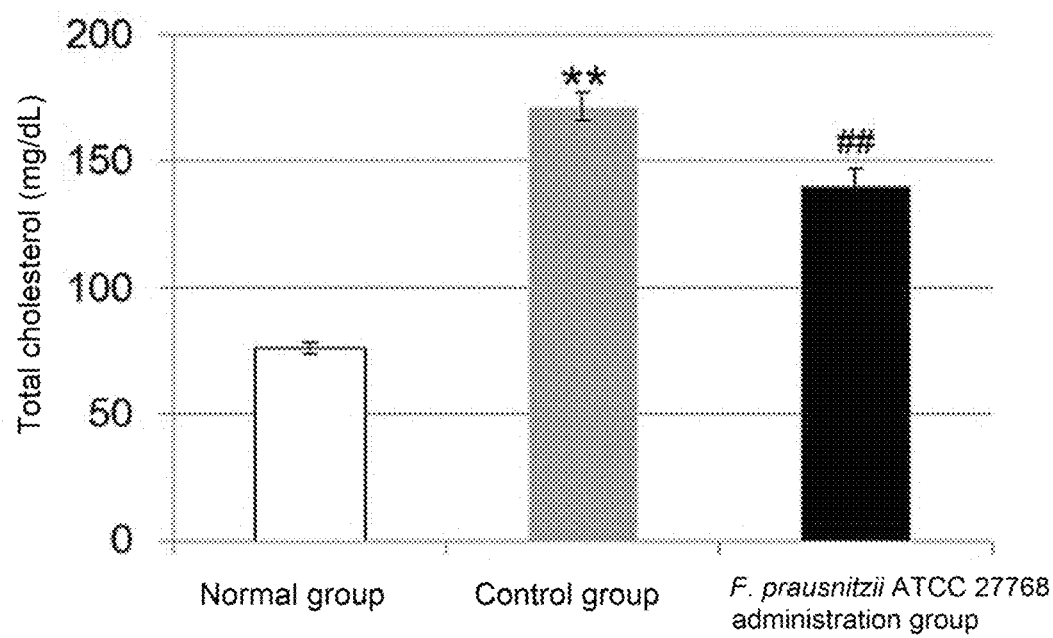
FIG. 6 is a chart showing the total cholesterol levels in the plasma of test animals in the normal group, the control group and the *F. prausnitzii* ATCC 27768 administration group.
Figure 7:
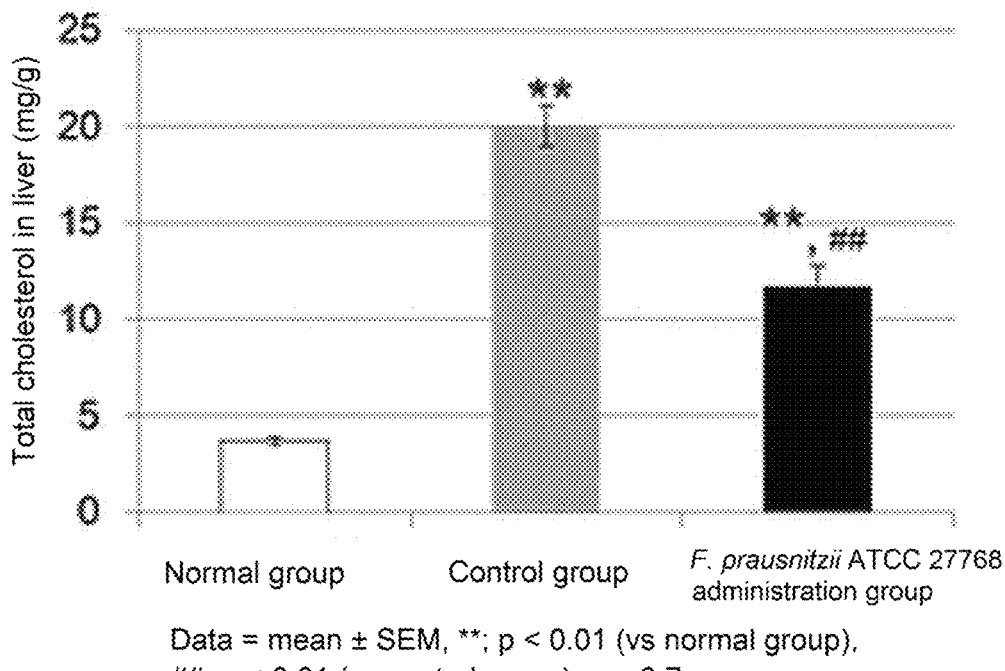
FIG. 7 is a chart showing the total cholesterol levels in the liver of test animals in the normal group, the control group and the *F. prausnitzii* ATCC 27768 administration group.
Figure 8:
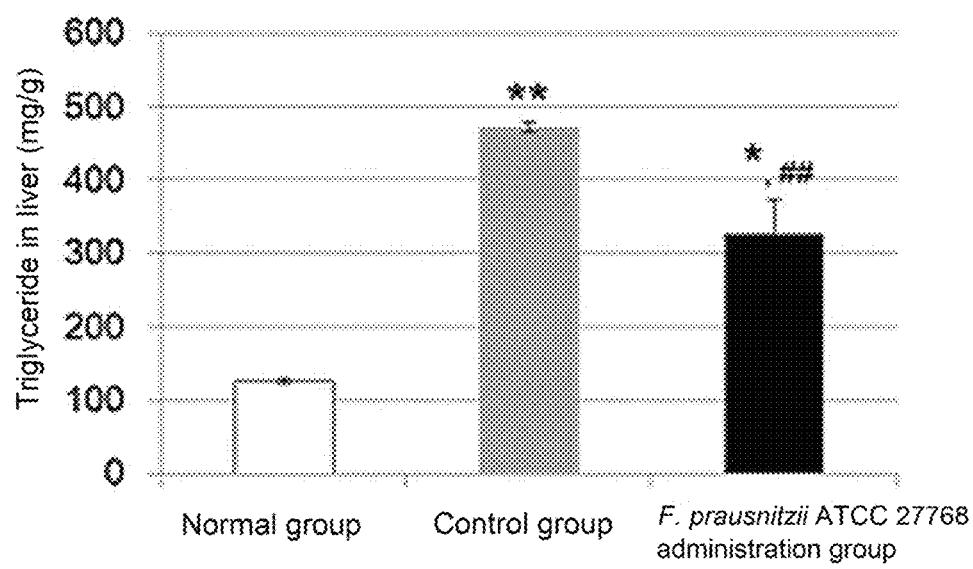
FIG. 8 is a chart showing the triglyceride levels in the liver of test animals in the normal group, the control group and the *F. prausnitzii* ATCC 27768 administration group.
Figure 9:
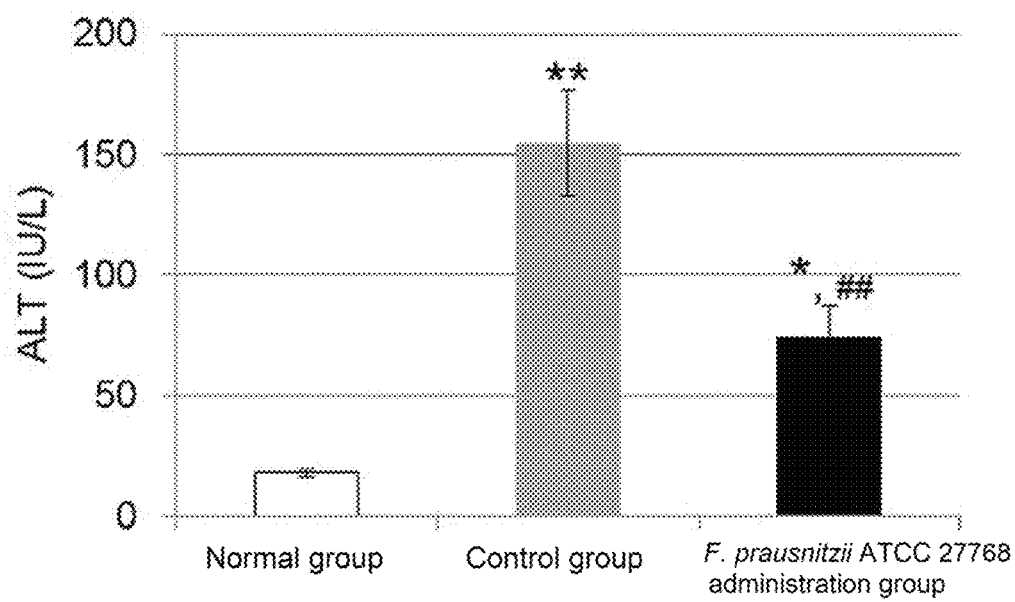
FIG. 9 is a chart showing the ALT levels in test animals in the normal group, the control group and the *F. prausnitzii* ATCC 27768 administration group.
Figure 10:
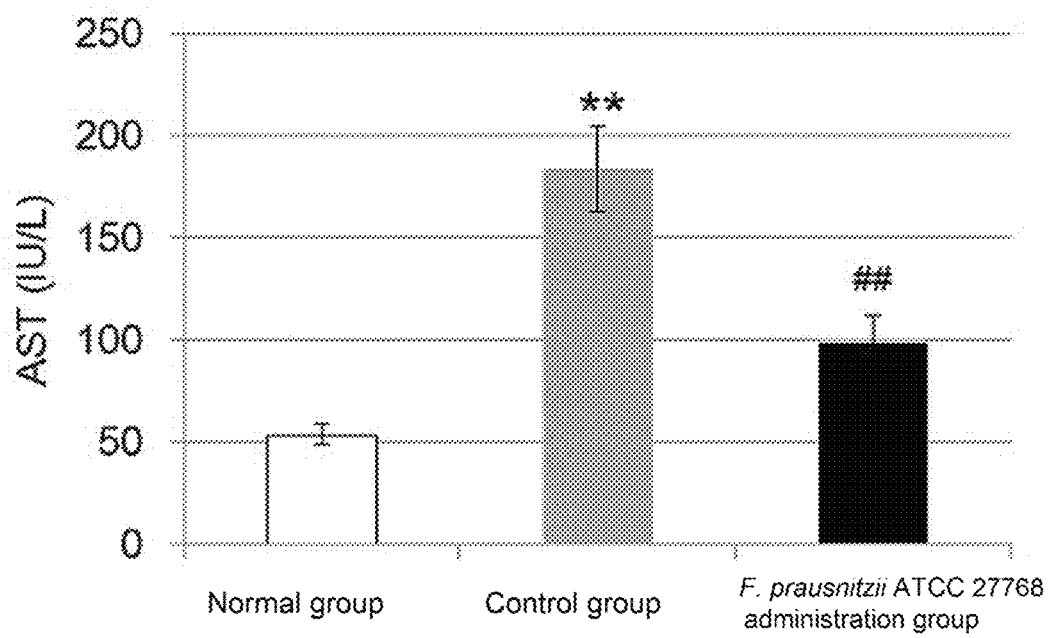
FIG. 10 is a chart showing the AST levels in test animals in the normal group, the control group and the *F. prausnitzii* ATCC 27768 administration group.
Figure 11:
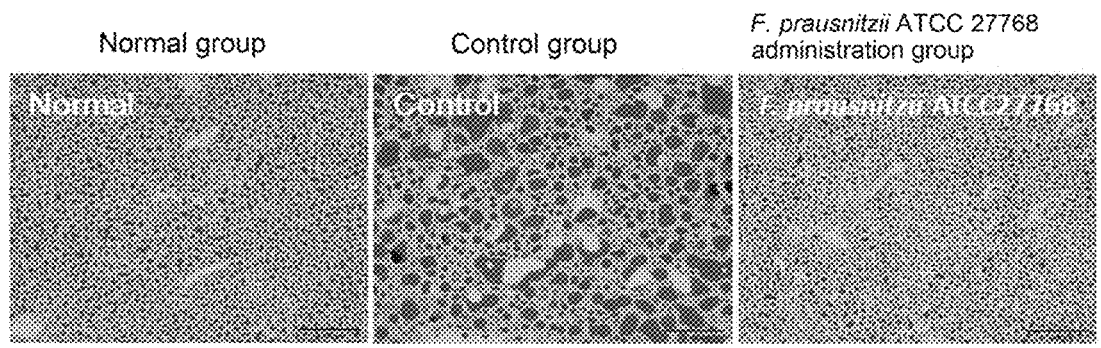
FIG. 11 shows photographs of oil red O staining of the histological sections of the liver of test animals in the normal group, the control group and the *F. prausnitzii* ATCC 27768 administration group.
Figure 12:
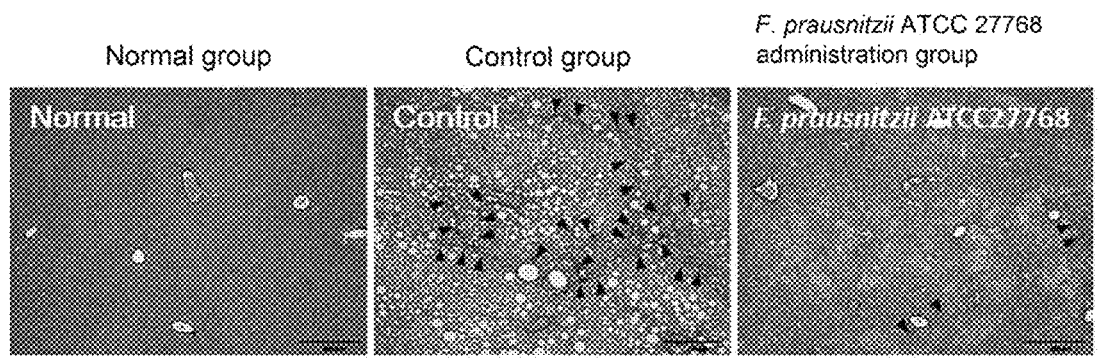
FIG. 12 shows photographs of Sirius red staining of the histological sections of the liver of test animals in the normal group, the control group and the *F. prausnitzii* ATCC 27768 administration group.
Figure 13:
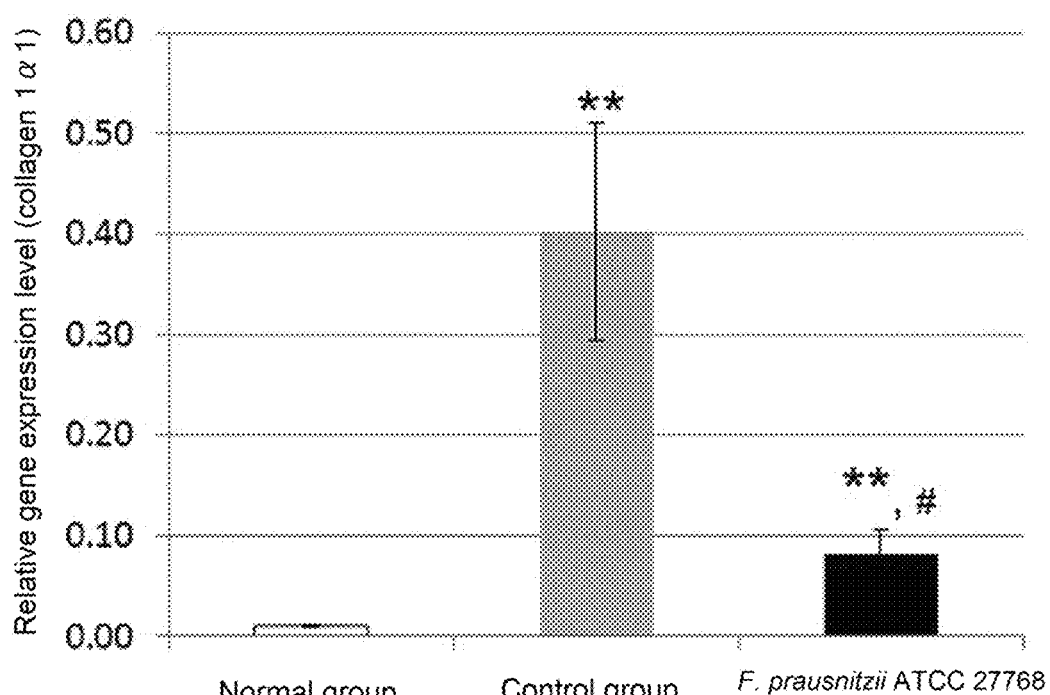
FIG. 13 is a chart showing the relative gene expression levels of collagen 1α1 in the liver of test animals in the normal group, the control group and the *F. prausnitzii* ATCC 27768 administration group.
Figure 14:
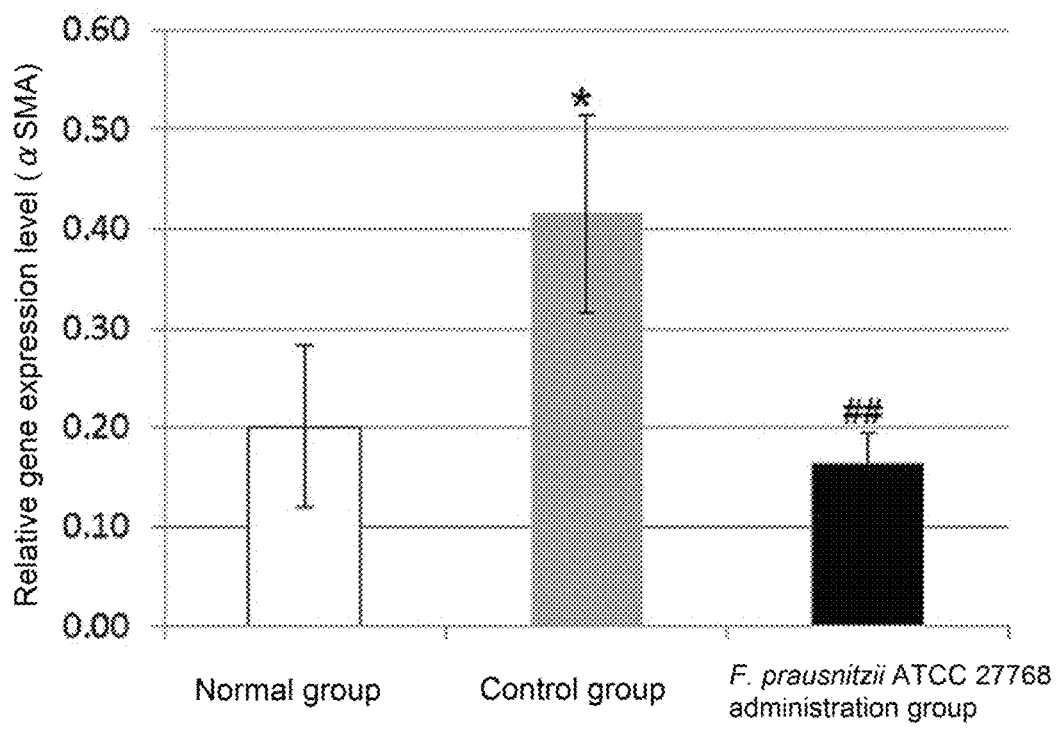
FIG. 14 is a chart showing the relative gene expression levels of αSMA in the liver of test animals in the normal group, the control group and the *F. prausnitzii* ATCC 27768 administration group.

The total cholesterol levels in the plasma, the total cholesterol levels in the liver and the triglyceride levels in the liver significantly decreased in the *F. prausnitzii* ATCC 27768 administration group as compared with the control group (FIGS. 6, 7 and 8). The ALT and AST levels, which are markers for liver functions, were significant improved by administration of *F. prausnitzii* ATCC 27768 (FIGS. 9 and 10). Administration of *F. prausnitzii* ATCC 27768 markedly reduced enlarged lipid droplets and collagen fibers in the liver as indicated by the arrowheads (FIGS. 11 and 12). Administration of *F. prausnitzii* ATCC 27768 also significantly reduced collagen 1α1, which is a factor that induces fibrosis in the liver, and significantly reduced the relative gene expression levels of αSMA, which indicates the activity of hepatic stellate cells, the cell type involved in fibrosis (FIGS. 13 and 14).

These results confirm that *F. prausnitzii* ATCC 27768 has inhibitory effect on fatty liver and/or liver fibrosis. The results also demonstrate that *F. prausnitzii* ATCC 27768 has liver function-improving effect, indicating that administration of *F. prausnitzii* ATCC 27768 inhibits the onset of the symptoms of NAFLD.

Example 5: Preventive or Therapeutic Effect on Inflammation Blood Chemistry Analysis In the same manner as in the blood chemistry analysis in Example 3, the plasma was separated from the whole blood withdrawn from the animals, and the plasma levels of endotoxin were measured with the measurement reagent LAL Chromogenic Endpoint Assay (Hycult Biotech Inc.).
Gene Expression Analysis The gene expression levels of IL-6 and 18S rRNA were measured by quantitative real-time PCR in the same manner as in the gene expression analysis in Example 4. The primers and probe for the IL-6 gene were those whose sequences are shown in Table 2. The gene expression levels of 18S rRNA were measured in the same manner as in the measurement of the gene expression levels of 18S rRNA in Example 4. The gene expression levels were evaluated by calculating the relative expression levels of the IL-6 gene normalized to that of 18S rRNA.

TABLE 2

| IL-6 | Probe | ACAATCAGAATTGCCATTGCACAACTCTTT | SEQ ID NO: 10 |
|---|---|---|---|
| | Forward | GTTCTCTGGGAAATCGTGGA | SEQ ID NO: 11 |
| | Reverse | TTCTGCAAGTGCATCATCGT | SEQ ID NO: 12 |

Results

Figure 15:
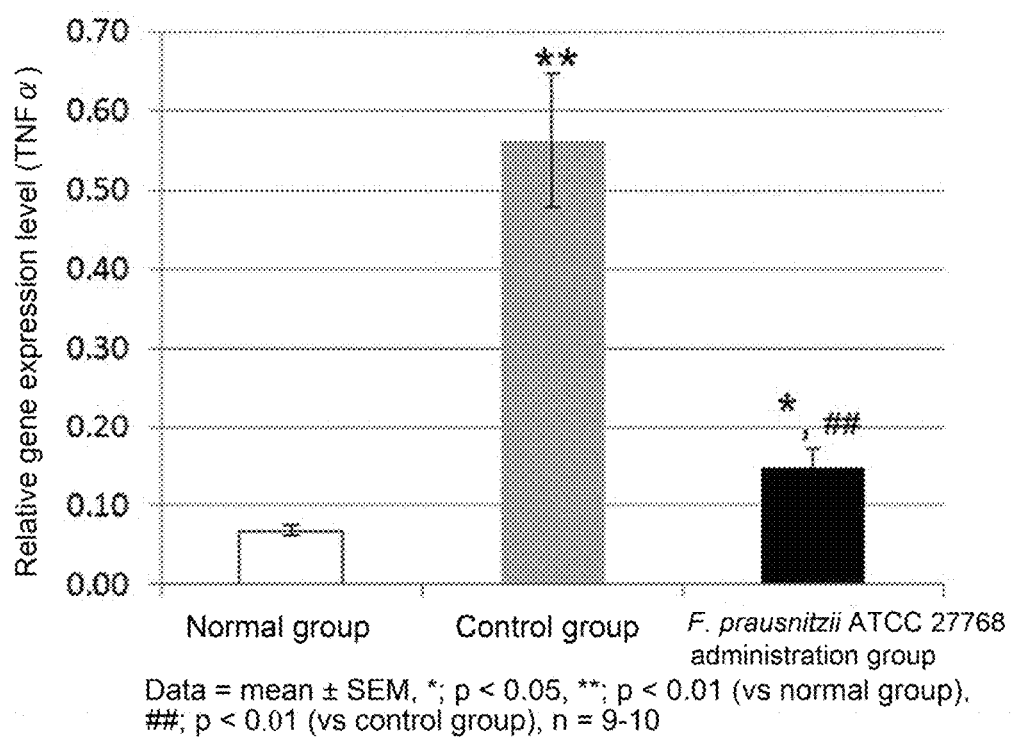
FIG. 15 is a chart showing the relative gene expression levels of TNFα in the liver of test animals in the normal group, the control group and the *F. prausnitzii* ATCC 27768 administration group.
Figure 16:
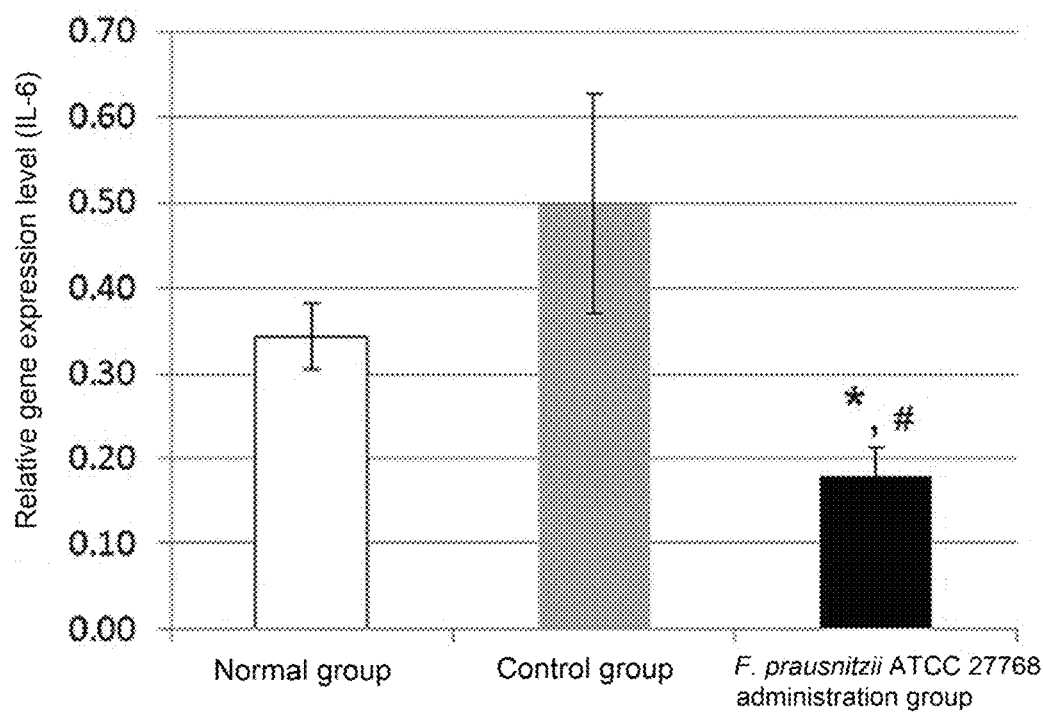
FIG. 16 is a chart showing the relative gene expression levels of IL-6 in the liver of test animals in the normal group, the control group and the *F. prausnitzii* ATCC 27768 administration group.
Figure 17:
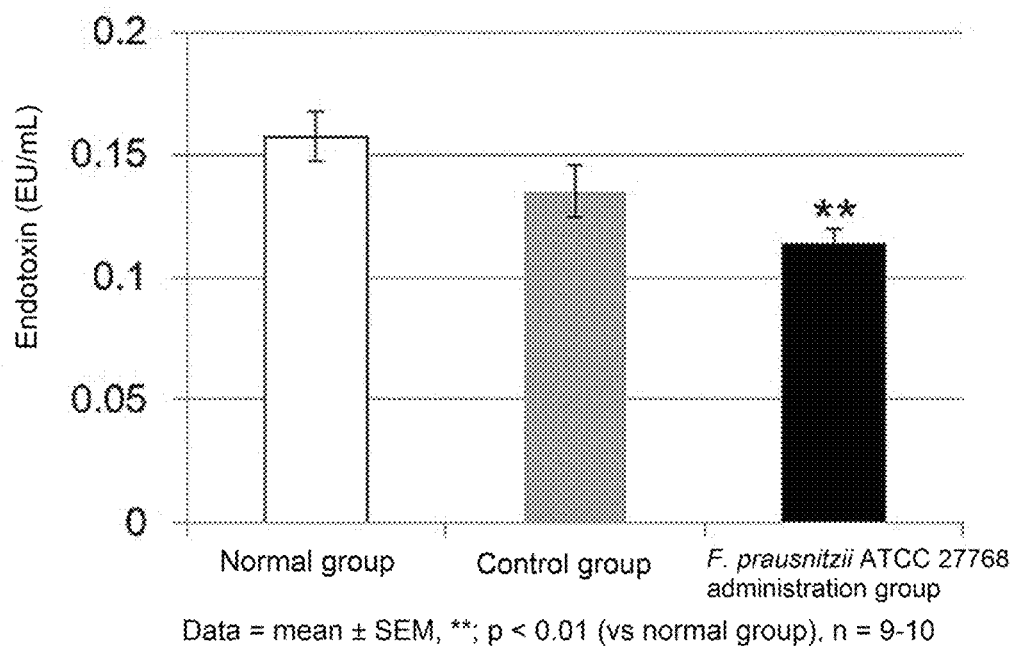
FIG. 17 is a chart showing the endotoxin levels in the plasma of test animals in the normal group, the control group and the *F. prausnitzii* ATCC 27768 administration group.

The relative gene expression levels of the proinflammatory cytokines TNFα and IL-6 significantly decreased in the *F. prausnitzii* ATCC 27768 administration group as compared with the control group (FIGS. 15 and 16). The plasma levels of endotoxin, which is absorbed from the intestinal tract and induces systemic inflammatory reaction, were significantly reduced by administration of *F. prausnitzii* ATCC 27768 as compared with the normal and control groups (FIG. 17). These results indicate that *F. prausnitzii* ATCC 27768 has anti-inflammatory effect.

Example 6: Preparation of Bacteria (*Faecalibacterium Prausnitzii* Reference Strain ATCC 27768 and *Faecalibacterium prausnitzii* TY-2 Strain)

Centrifuged bacterial cells of the *Faecalibacterium prausnitzii* reference strain ATCC 27768 (*F. prausnitzii* ATCC 27768) and the *Faecalibacterium prausnitzii* TY-2 strain (*F. prausnitzii* TY-2) (Accession No. NITE BP-02743) were prepared. Specifically, a cryopreserved strain of *F. prausnitzii* ATCC 27768 or *F. prausnitzii* TY-2 was subjected to stationary culture at 37° C. for 48 hours. The bacteria were inoculated into the tryptic soy broth B at a 1:100 volume ratio of the bacteria to the bacterial culture broth, and stationary culture was performed at 37° C. for 48 hours. The bacterial culture broth was centrifuged, and the bacterial pellet was washed twice with PBS, and centrifuged to give centrifuged bacterial cells.

Example 7: Preparation of Dead Bacterial Cells

Centrifuged bacterial cells of the *Faecalibacterium prausnitzii* reference strain ATCC 27768 (*F. prausnitzii* ATCC 27768) or the *Faecalibacterium prausnitzii* TY-2 strain (*F. prausnitzii* TY-2) (Accession No. NITE BP-02743) were irradiated with γ-rays at 30 kGy for about 190 minutes to prepare dead bacterial cells. The irradiation was done by the external company Koga Isotope Ltd.

Experimental Example B: Test Animals and Administration of Bacteria

C57BL/6J mice at 8 weeks old were given a high-fat high-fructose diet (may also be called AMLN diet; Research Diets, Inc.) and also orally given non-γ-ray irradiated *F. prausnitzii* ATCC 27768, γ-ray irradiated *F. prausnitzii* ATCC 27768, non-γ-ray irradiated *F. prausnitzii* TY-2 or γ-ray irradiated *F. prausnitzii* TY-2 at a dose of 20 mg/animal once a day for 20 weeks. The normal group was given an ordinary diet (MF diet, Oriental Yeast Co., Ltd.) with no administration of *F. prausnitzii* ATCC 27768 or *F. prausnitzii* TY-2. The control group was given the high-fat high-fructose diet with no administration of *F. prausnitzii* ATCC 27768 or *F. prausnitzii* TY-2.

Example 8: Inhibitory Effect on Liver Fibrosis

Pathological Analysis

The liver was harvested from the test animals, fixed by immersing in 10% formalin, embedded in paraffin to create a paraffin block, and sectioned into paraffin sections, according to conventional methods. The paraffin sections of the liver were stained with Sirius red stain solution (Sigma-Aldrich Japan G.K.) according to the attached protocol. The stained paraffin sections were photographed.

Results

Figure 18:
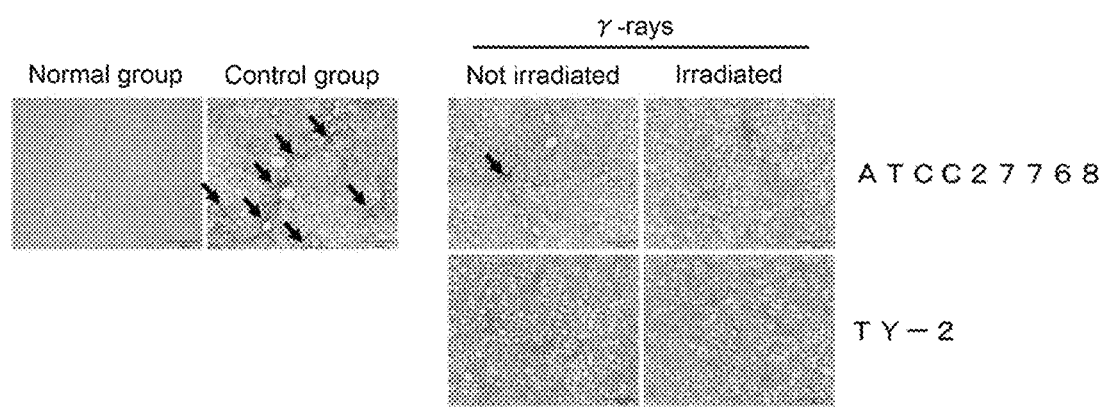
FIG. 18 shows photographs showing the degree of fibrosis in the liver of test animals in the normal group, the control group, the *F. prausnitzii* ATCC 27768 administration group, and the *F. prausnitzii* TY-2 administration group.

Collagen fibers in the liver were markedly reduced by administration of any of the non-γ-ray irradiated *F. prausnitzii* ATCC 27768, the γ-ray irradiated *F. prausnitzii* ATCC 27768, the non-γ-ray irradiated *F. prausnitzii* TY-2 and the γ-ray irradiated *F. prausnitzii* TY-2, as indicated by the arrowheads (FIG. 18).

These results confirm that the non-γ-ray irradiated *F. prausnitzii* ATCC 27768, the γ-ray irradiated *F. prausnitzii* ATCC 27768, the non-γ-ray irradiated *F. prausnitzii* TY-2 strain and the γ-ray irradiated *F. prausnitzii* TY-2 strain have inhibitory effect on liver fibrosis. That is, the results confirm that viable cells and dead cells of *Faecalibacterium* bacteria have inhibitory effect on liver fibrosis.

INDUSTRIAL APPLICABILITY

The present invention prevents or treats obesity-associated diseases and/or inflammation and is thus useful for prevention or treatment of metabolic syndrome etc.

The invention claimed is:

1. A formulation comprising an effective amount of (i) *Faecalibacterium prausnitzii* TY-2 having the Accession No. NITE BP-02743 or a processed product thereof and (ii) a pharmaceutically acceptable base material, carrier or additive, a physiologically active ingredient, or a pharmacologically acceptable active ingredient, wherein the processed product is selected from the group consisting of viable cells, dead cells, sonicated cells, concentrates, dried cells, and disrupted cells of the *Faecalibacterium prausnitzii* TY-2.

2. A composition comprising an effective amount of (i) *Faecalibacterium prausnitzii* TY-2 having the accession number NITE BP-02743 or a processed product thereof and (ii) a pharmaceutically acceptable base material, carrier or additive, a physiologically active ingredient, or a pharmacologically acceptable active ingredient, wherein the processed product is selected from the group consisting of viable cells, dead cells, sonicated cells, concentrates, dried cells, and disrupted cells of the *Faecalibacterium prausnitzii* TY-2.

3. The composition of claim 2, wherein the composition is selected from fermented foods, drinks, confectionaries, seasonings, bread, noodles, steamed fish paste, and rice seasonings.

4. The composition of claim 2, wherein said composition is a pharmacological composition or a food composition.

5. The formulation of claim 1, wherein the formulation is selected from fermented foods, drinks, confectionaries, seasonings, bread, noodles, steamed fish paste, and rice seasonings.

6. The composition of claim 2, wherein the composition is in the form of a powder, a capsule, a granule, a tablet, or a liquid food.

7. A method of inhibiting liver fibrosis in a mammalian subject, the method comprising oral administration of an effective dose of the composition of claim 2.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: Probe

<400> SEQUENCE: 1
cccgccgatg tcgctatcca gct                                    23

<210> SEQ ID NO 2
<211> LENGTH: 20
<212> TYPE: DNA
<213> ORGANISM: Artificial
<220> FEATURE:

```
<223> OTHER INFORMATION: Primer

<400> SEQUENCE: 2
gaccgatgga ttcccgttcg                                              20

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
ggacattagg cgcaggaagg                                              20

<210> SEQ ID NO 4
<211> LENGTH: 25
<212> TYPE: DNA
<213> ORGANISM: Artificial
<220> FEATURE:
<223> OTHER INFORMATION: Probe

<400> SEQUENCE: 4
cccagagtgg agaagcccag ccagt                                        25

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
acccttcagc gttcagcctc                                              20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
cacacatagc tggagcagcg                                              20

<210> SEQ ID NO 7
<211> LENGTH: 26
<212> TYPE: DNA
<213> ORGANISM: Artificial
<220> FEATURE:
<223> OTHER INFORMATION: Probe

<400> SEQUENCE: 7
aggggccacc acgctcttct gtctac                                       26

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
gcctatgtct cagcctcttc tc                                           22
```

```
<210> SEQ ID NO 9
<211> LENGTH: 23
<212> TYPE: DNA
<213> ORGANISM: Artificial
<220> FEATURE:
<223> OTHER INFORMATION: Primer

<400> SEQUENCE: 9
aggccatttg ggaacttctc atc                                              23

<210> SEQ ID NO 10
<211> LENGTH: 30
<212> TYPE: DNA
<213> ORGANISM: Artificial
<220> FEATURE:
<223> OTHER INFORMATION: Probe

<400> SEQUENCE: 10
acaatcagaa ttgccattgc acaactcttt                                       30

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gttctctggg aaatcgtgga                                                  20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
ttctgcaagt gcatcatcgt                                                  20
```